United States Patent [19]

Thenot et al.

[11] Patent Number: 5,620,990
[45] Date of Patent: Apr. 15, 1997

[54] ALPHA-(4-CHLOROPHENYL)-4-[(4-FLUORPHENYL)-METHYL]PIPERIDINE-1-ETHANOL ESTERS, THEIR PREPARATION AND THEIR THERAPEUTIC APPLICATION

[75] Inventors: Jean P. Thenot, Gif sur Yvette; Jonathan Frost, Wissous; Patrick Lardenois, Bourg la Reine; Maria C. Renones, Enghien les Bains; Alexander Wick, Saint Nom la Breteche, all of France

[73] Assignee: Synthelabo, Le Plessis Robinson, France

[21] Appl. No.: 499,918

[22] Filed: Jul. 11, 1995

[30] Foreign Application Priority Data

Jul. 13, 1994 [FR] France .................... 94 08711

[51] Int. Cl.⁶ .................... A61K 31/445; C07D 211/34; C07D 211/08
[52] U.S. Cl. .................... 514/317; 546/192; 546/239
[58] Field of Search .................... 546/239, 192; 514/317

[56] References Cited

U.S. PATENT DOCUMENTS

| | | | |
|---|---|---|---|
| 4,690,931 | 9/1987 | Wick et al. | 514/317 |
| 5,395,841 | 3/1995 | Foguet et al. | 514/317 |
| 5,434,171 | 7/1995 | Frank et al. | 514/317 |

FOREIGN PATENT DOCUMENTS

| | | |
|---|---|---|
| 2628740 | 9/1989 | France . |
| 2694555 | 11/1994 | France . |

*Primary Examiner*—C. Warren Ivy
*Assistant Examiner*—Raymond Covington
*Attorney, Agent, or Firm*—Jacobson, Price, Holman & Stern, PLLC

[57] ABSTRACT

The present invention provides a piperidine derivative of formula (I)

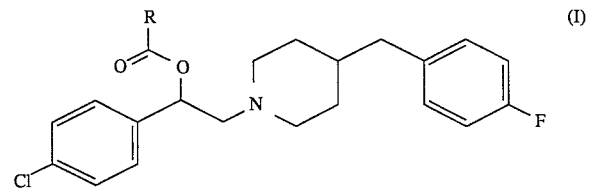

in which R represents a straight- or branched-chain $(C_1-C_{19})$alkyl group, a straight- or branched-chain $(C_2-C_{19})$alkenyl group, a $(C_3-C_6)$cycloalkyl group, a cycloalkylmethyl group in which the cycloalkyl moiety has from three to six carbon atoms, a phenyl group which is optionally substituted by a halogen atom or a phenyl methyl group which is optionally substituted by a halogen atom, or an addition salt thereof, in the form of an optically pure enantiomer or of a mixture of enantiomers, a process for making them and their therapeutic application.

8 Claims, No Drawings

ALPHA-(4-CHLOROPHENYL)-4-[(4-FLUORPHENYL)-METHYL]PIPERIDINE-1-ETHANOL ESTERS, THEIR PREPARATION AND THEIR THERAPEUTIC APPLICATION

The present invention provides a piperidine derivative of formula (I)

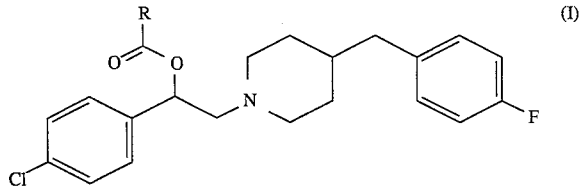

in which

R represents a straight- or branched-chain ($C_1$–$C_{19}$) alkyl group, a straight- or branched-chain ($C_2$–$C_{19}$) alkenyl group, a ($C_3$–$C_6$) cycloalkyl group, a cycloalkylmethyl group in which the cycloalkyl moiety has from three to six carbon atoms, a phenyl group which is optionally substituted by a halogen atom or a phenyl methyl group which is optionally substituted by a halogen atom, or an addition salt thereof, in the form of an optically pure enantiomer or of a mixture of enantiomers.

Preferred are compounds of formula (I) in which R represents a straight- or branched-chain ($C_1$–$C_{17}$) alkyl group, a straight- or branched-chain ($C_2$–$C_{17}$) alkenyl group, a $C_5$ or $C_6$ cycloalkyl group, a cycloalkylmethyl group in which the cycloalkyl moiety has five or six carbon atoms, a phenyl group which is optionally substituted by a fluorine atom, or a phenyl methyl group in which the phenyl moiety is optionally substituted by a fluorine atom.

More preferred are compounds of formula (I) in which R represents methyl, hexyl, decyl, isopropyl, tertiary-butyl, cyclopentyl, cyclopentylmethyl, 4-fluorophenyl, 4-fluorophenylmethyl, $CH_3(CH_2)_{16}$— or cis-$CH_3(CH_2)_7CH$=$CH(CH_2)_7$—.

In the compounds of the invention, one of the carbon atoms is asymmetric; they can therefore exist in the form of optically pure enantiomers or of mixtures of enantiomers. Moreover, they can be provided in the form of free bases or of addition salts.

Preferred addition salts are the hydrochloride, (E)-but-2-enedioate or ethanedioate salts.

The present invention also provides a process for preparing a compound of formula (I), in which α-(4-chlorophenyl)-4-[(4-fluorophenyl)-methyl]piperidine-1-ethanol, of formula (II)

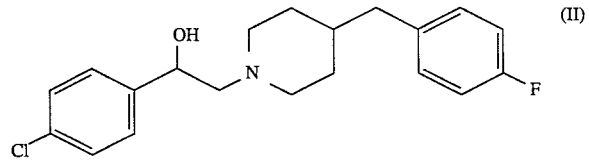

is reacted with an anhydride of formula $(RCO)_2O$ or an acid chloride of formula RCOCl, in which R is as defined above. The reaction conditions are well known for esterification reactions.

The compound of formula (II) and its enantiomers are described EP-B-109,317 and FR-B-2,268,740.

The acid anhydrides of formula $(RCO)_2O$ and the acid chlorides of formula RCOCl are commercially available or alternatively can be prepared from the corresponding acids according to any known methods. For example, the acid chlorides can be prepared by the action of thionyl chloride on the corresponding carboxylic acid.

The following examples illustrate in detail the preparation of a few compounds according to the invention. Elemental microanalyses and IR and NMR spectra confirm the structures of the compounds obtained.

The numbers of the compounds which are indicated in brackets in the titles correspond to those of the table given later.

EXAMPLE 1

(Compound No. 1)

(±)-α-(4-chlorophenyl)-4-[(4-fluorophenyl)methyl]-piperidine-1-ethyl acetate (E)-but-2-enedioate (1:1).

3.47 g (0.01 mole) of (±)-α-(4 chlorophenyl)-4-[(4-fluorophenyl)methyl]-piperidine-1-ethanol and 20 ml of acetic anhydride are placed in a 250 ml round-bottomed flask and the mixture is stirred at room temperature overnight.

The excess of anhydride is evaporated, the residue is taken up with 100 ml of ethyl acetate, an excess of 3N ammonium hydroxide is added, the organic phase is separated, the aqueous phase is extracted with ethyl acetate, the organic phases are combined, they are washed with water, they are dried over sodium sulphate, the solvent is evaporated under reduced pressure and 4.5 g of an oily product are obtained which are purified by chromatography on a silica gel column, eluted with a 98/2 mixture of dichloromethane/methanol.

The purified fraction is dissolved in ethanol and the fumarate is prepared with one equivalent of fumaric acid.

After two recrystallizations from ethanol and one recrystallization from propan-2-ol, then drying, 0.89 g of compound is finally obtained. Melting point: 164°–165° C.

EXAMPLE 2

(Compound No. 2)
R-(−)-α-(4-chlorophenyl)-4-[(4-fluorophenyl)methyl]piperidine-1-ethyl acetate.

2.62 g (0.00753 mole) of R-(−)-α-(4-chlorophenyl)-4-[(4-fluorophenyl)methyl]piperidine-1-ethanol and 15 ml of acetic anhydride are introduced into a 50 ml round-bottomed flask and the mixture is stirred at room temperature overnight.

The mixture is poured over ice-cold water, stirred for 1 h and ammonium hydroxide is added. A whitish oily product is formed which solidifies. It is separated and dried in the presence of phosphorus pentoxide, which gives 2.77 g of solid.

After recrystallization from propan-2-ol and drying, 1.87 g of levorotatory compound are obtained.

Melting point: 73°–74° C.

$[\alpha]_D^{25}$=−43.8° (c=1; $CHCl_3$).

EXAMPLE 3

(Compound No. 3)
S-(+)-α-(4-chlorophenyl)-4-[(4-fluorophenyl)methyl]piperidine-1-ethyl acetate.

Using the method described in the preceding example, 2.35 g of dextrorotatary compound are obtained from 3.16 g (0.0098 mole) of S-(+)-α-(4-chlorophenyl)-4-[(4-fluorophenyl)methyl]piperidine-1-ethanol.

Melting point: 73°–74° C.

$[\alpha]_D^{25}$=+42.0° (c=1; $CHCl_3$).

EXAMPLE 4

(Compound No. 5)

(±)-α-(4-chlorophenyl)-4-[(4-fluorophenyl)methyl]-piperidine-1-ethyl undecanoate (E)-but-2-enedioate (1:1).

4.65 g (0.025 mole) of undecanoic acid are introduced into a round-bottomed flask, 3.5 g (0.03 mole) of thionyl chloride are added and the mixture is heated on an oil bath at 60° C. for 2 h. The excess of thionyl chloride is evaporated under reduced pressure and the traces are removed by entrainment with toluene, the residue is cooled using an ice bath, a solution of 7 g (0.02 mole) of (±)-α-(4-chlorophenyl)-4-[(4-fluorophenyl)methyl]piperidine-1-ethanol in 50 ml of pyridine is added dropwise, the bright yellow mixture is stirred for 30 min and it is left at room temperature overnight.

The solvent is evaporated under reduced pressure and the residue is purified by chromatography on a silica gel column, eluting with ethyl acetate. 4 g of a thick oil are obtained which are dissolved in 25 ml of ethanol, 1 g of fumaric acid is added, and the solution is placed in the cold for 2 d.

50 ml of petroleum ether are added to the crystalline mass, the mixture is stirred for 15 min and the white precipitate separated by filtration. After recrystallization from propan-2-ol, 0.86 g of compound is obtained.

Melting point:144°–145° C.

EXAMPLE 5

(Compound No. 9)

(±)-α-(4-chlorophenyl)-4-[(4-fluorophenyl)methyl]piperidine-1-ethyl cyclopentaneacetate (E)-but-2-enedioate (1:1).

3.8 g (0.03 mole) of cyclopentaneacetic acid and 12 g (0.1 mole) of thionyl chloride are placed in a 250 ml round-bottomed flask provided with a calcium chloride tube, a drop of N,N-dimethylformamide is added and the mixture is heated on an oil bath at 60° C. for 3 h.

The mixture is stirred at room temperature overnight and the excess of thionyl chloride is removed by evaporation and then by entrainment with toluene. A clear oil is obtained which is diluted with 5 ml of toluene, the latter is poured, dropwise, into a round-bottomed flask containing 3.47 g (0.01 mole) of (±)-α-(4-chlorophenyl)-4-[(4-fluorophenyl)methyl]piperidine-1-ethanol dissolved in 15 ml of pyridine, and the mixture is stirred at room temperature overnight. The solvents are evaporated under reduced pressure and the traces of pyridine are removed by entrainment with water, the residue is taken up in water and ethyl acetate, the organic phase is separated, the aqueous phase is extracted twice with ethyl acetate, the organic phases are combined, they are dried over sodium sulphate and the solvent is evaporated under reduced pressure.

7.9 g of an oily product are obtained which are exhaustively extracted with first cold then boiling isopropyl ether, the organic phases are combined, a cloudiness is removed by filtration on paper, the isopropyl ether is evaporated under reduced pressure and the residue is purified by chromatography on a silica gel column, eluting with isopropyl ether. 3.14 g of an oily product are obtained of which the fumarate is prepared in ethanol with one equivalent of fumaric acid.

After recrystallization from 25 ml of propan-2-ol and drying, 1.94 g of fumarate are finally obtained.

Melting point: 146°–147° C.

The table below illustrates the chemical structures and the physical properties of a few compounds according to the invention. In the "R" column, "$cC_5H_9-$" designates a cyclopentyl group and "$4-F-C_6H_4-$" designates a 4-fluorophenyl group. In the "salt" column, "—" designates a compound in the form of a base, "fum." designates an (E)-but-2-enedioate (1:1) (fumarate), "HCl" designates a hydrochloride (1:1) and "ox." designates an ethanedioate (1:1) (oxalate).

TABLE

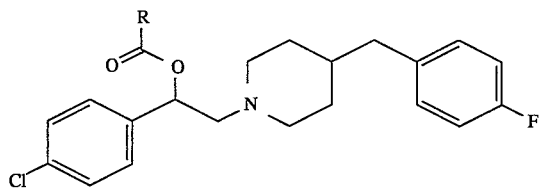

(I)

| No. | R | Isomer | Salt | m.p. (°C.) | $[\alpha]_D^{25}$ (c = 1) |
|---|---|---|---|---|---|
| 1 | $CH_3-$ | (±) | fum. | 164–165 | — |
| 2 | $CH_3-$ | R (−) | — | 73–74 | −43.8° (CHCl$_3$) |
| 3 | $CH_3-$ | S (+) | — | 73–74 | +42.0° (CHCl$_3$) |
| 4 | $CH_3-(CH_2)_5-$ | (±) | fum. | 159–160 | — |
| 5 | $CH_3-(CH_2)_9-$ | (±) | fum. | 144–145 | — |
| 6 | $(CH_3)_2CH-$ | (±) | fum. | 173–174 | — |
| 7 | $(CH_3)_3C-$ | (±) | fum. | 181–182 | — |
| 8 | $cC_5H_9-$ | (±) | fum. | 169–170 | — |
| 9 | $cC_5H_9-CH_2-$ | (±) | fum. | 146–147 | — |
| 10 | $4-F-C_6H_4-$ | (±) | fum. | 197–198 | — |
| 11 | $4-F-C_6H_4-CH_2-$ | (±) | HCl | 195–196 | — |
| 12 | $CH_3(CH_2)_{16}-$ | (±) | fum. | 115–116 | — |
| 13 | $CH_3(CH_2)_{16}-$ | R (−) | fum. | 116–118 | −28.9° (CH$_3$OH) |
| 14 | $CH_3(CH_2)_{16}-$ | S (+) | fum. | 116–118 | +26.7° (CH$_3$OH) |
| 15 | cis-$CH_3(CH_2)_7CH=CH(CH_2)_7-$ | (±) | ox. | 119–120 | — |
| 16 | cis-$CH_3(CH_2)_7CH=CH(CH_2)_7-$ | R (−) | ox. | 99–100 | −27.5° (CH$_3$OH) |
| 17 | cis-$CH_3(CH_2)_7CH=CH(CH_2)_7-$ | S (+) | ox. | 99–100 | +26.5° (CH$_3$OH) |

The compounds of the invention were subjected to trials which demonstrated their neuroprotective and neurotrophic activity.

Consequently, they have been the subject of a trial for inhibiting the binding of [$^3$H] ifenprodil to the modulatory sites sensitive to the polyamines of the NMDA receptor complex in rat cerebral cortex membranes, according to the procedure described by Schoemaker et al., *Eur. J. Pharmacol.* (1990) 176 249–250. Male Sprague-Dawley rats of 150 to 230 g are sacrificed and the cerebral cortex is homogenized in 20 volumes of ice-cold Tris-HCl buffer at 50 mM (pH=7.4 at 0° C.) by means of an Ultra-Turax™ (Ikawerk) or Polytron™ (Kinematica) apparatus. The homogenate is washed twice by centrifugation for 10 min at 45,000×g, the pellet being resuspended in fresh buffer. The final pellet is taken up in 20 volumes of the same buffer.

A 100 µl aliquot of this suspension is incubated in a final volume of 1000 µl with 1 nM [$^3$H]ifenprodil (specific activity: 30 to 35 Ci/mmol) for 120 min at 0° C., in the presence of 3 µM GBR 12909 (Research Biochemicals Inc., Natick, Mass., USA), in the absence or in the presence of competitor substance.

After incubation, the mixture is diluted with 5 ml of ice-cold buffer Tris-HCl at 50 mM (pH=7.4 at 0° C.) and the membranes are recovered by filtration on Whatman GF/B™ filters pretreated with polyethyleneimine at 0.05%, and then washed with twice 5 ml of ice-cold buffer.

The nonspecific binding with 10 µM ifenprodil is determined, the data are analysed according to the customary methods and the $IC_{50}$ concentration, a concentration which inhibits by 50% the binding of [$^3$H]ifenprodil, is calculated.

The $IC_{50}$ values of the most active compounds in this trial are of the order of 0.4 µM.

The affinity of the compounds of the invention for a [$^3$H]ifenprodil binding site not associated with the NMDA receptors and having analogies with the $\sigma_2$ sites was also evaluated.

Male Sprague-Dawley rats, with a weight of 150 to 230 g, are sacrificed and the cerebral cortex is homogenized at 4° C. in 20 volumes of ice-cold Tris-HCl buffer 50 mM, pH=7.4, by means of an Ultra-Turax™ (Ikawerk) or Polytron™ (Kinematica) apparatus. After centrifugation for 10 min at 45,000×g, the supernatant is removed and the pellet again washed under the same conditions and then resuspended in the starting buffer volume.

Aliquots of 100 µl of suspension of membranes are incubated for 30 min at 37° C. in i ml of buffer containing the compounds to be tested and 0.5 nM [$^3$H]ifenprodil. Nonspecific binding is determined in the presence of 10 µM ifenprodil. The bound radioactivity is separated by filtration on Whatman GF/B™ filters previously treated with polyethyleneimine at 0.05% and then washed twice with 5 ml of ice-cold buffer. The results are analysed according to the customary methods, and the concentration which inhibits by 50% the binding of [$^3$H]ifenprodil is calculated. The $IC_{50}$ values of the most active compounds in this test range from 0.04 to 0.4 µM.

Finally, the compounds of the invention were subjected to the test of global cerebral ischemia in mice. The ischemia is caused by a cardiac arrest induced by a rapid intravenous injection of magnesium chloride. In this test, the "survival time" that is to say the interval between the time of injecting magnesium chloride and the last observable respiratory movement of each mouse, is measured. This last movement is considered as the final indication of a central nervous system function.

Respiratory arrest appears approximately 19 seconds after the injection of magnesium chloride in the control mice.

Male mice (Charles River CD1) are studied in groups of 10. They are fed and provided with water ad libitum before the trials. The survival time is measured 10 min after intraperitoneal administration of the compounds of the invention. The difference between the survival time measured in a group of 10 mice having received the study compound and the survival time measured in a group of 10 mice having received the vehicle liquid is calculated.

The extensions of the survival time as a function of the dose of the compound are expressed graphically by means of a semilogarithmic curve.

This curve makes it possible to calculate the "3 second effective dose" ($ED_{3''}$), that is to say the dose (in mg/kg) which produces an increase of 3 seconds in the survival time relative to the control group of untreated mice.

An increase of 3 seconds in the survival time is both statistically significant and reproducible.

The $ED_{3''}$ values of the most active compounds in this trial are of the order of 3 mg/kg intraperitoneally.

The results of the trials carried out suggest that the compounds of the invention possess neuroprotective and neurotrophic activities.

These activities may find application in the treatment and the prevention of neurological disorders such as those which follow for example an ischemic attack, a cardiac or respiratory arrest, a cerebral thrombosis or emboly or a cranial or medullary trauma. The compounds of the invention can also be used for the treatment of cerebral senility, of dementia resulting from multiple infarcts, of vascular dementia, of multiple sclerosis, for the treatment of olivopontocerebellar atrophy and of other neurodegenerative diseases, for example Alzheimer's disease, Pick's disease and Huntington's chorea.

They can also be used for the treatment of peripheral neuropathies of the trauma, ischemic, metabolic, infectious, alcoholic, iatrogenic or genetic type, for the treatment of diseases affecting the motoneurons, such as amyotrophic lateral sclerosis and amyotrophies. In patients suffering from glaucoma, they can serve for the prevention of degeneration of the optic nerve or of the retina.

Finally, their use may be envisaged in the treatment of convulsive states, the treatment of migraine, the treatment of acquired tolerance and/or of addiction to narcotic analgesics, and as antiemetics.

The compounds of the invention can be used alone or in combination with other therapeutic substances, for example with a thrombolytic agent such as a recombinant tissue plasminogen activator, for the treatment of thromboembolic type cerebral infarcts, or with a compound which decreases intraocular pressure, for the treatment of glaucoma, or alternatively with an anticancer agent, for the purpose of reducing the side effects (neuropathies and the like) of the latter.

To this end, there may be provided in any pharmaceutical forms suitable for enteral or parenteral administration, in combination with appropriate excipients, for example in the form of tablets, sugar-coated tablets, gelatin capsules, capsules, suppositories, patches, solutions or suspensions to be taken orally or injected, compositions comprising a compound of the present invention, in doses which allow a daily administration of 1 to 1000 mg of active substance.

The present invention also provides a pharmaceutical composition which comprises a compound of the present invention in association with an excipient.

The present invention provides a compound of the present invention for use in a method of treatment of the human or animal body.

The present invention further provides the use of a compound of the present invention in the manufacture of a medicament for use as a neuroprotective or neurotrophic agent.

The compounds of the present invention can be used in a method of treating a subject requiring the administration of a neuroprotective or neurotrophic agent which comprises administering to that subject an effective amount of a compound of the present invention.

The present invention further provides a neuroprotective or neurotrophic composition comprising a compound of the present invention and a pharmaceutically acceptable adjuvant.

We claim:

1. A piperidine derivative of formula (I)

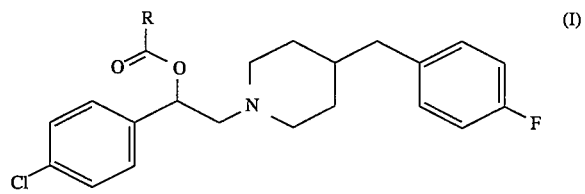

in which R represents a straight- or branched-chain ($C_1$–$C_{19}$) alkyl group, a straight- or branched-chain ($C_2$–$C_{19}$)alkenyl group, a ($C_3$–$C_6$)cycloalkyl group, a cycloalkylmethyl group in which the cycloalkyl moiety has from three to six carbon atoms, a phenyl group which is optionally substituted by a halogen atom or a phenyl methyl group which is optionally substituted by a halogen atom, or an addition salt thereof, in the form of an optically pure enantiomer or of a mixture of enantiomers.

2. A compound according to claim 1, in which R represents a straight- or branched-chain ($C_1$–$C_{17}$) alkyl group, a straight- or branched-chain ($C_2$–$C_{17}$) alkenyl group, a $C_5$ or $C_6$ cycloalkyl group, a cycloalkylmethyl group in which the cycloalkyl moiety has five or six carbon atoms, a phenyl group which is optionally substituted by a fluorine atom or a phenyl methyl group which is optionally substituted by a fluorine atom.

3. A compound according to claim 2, in which R represents methyl, hexyl, decyl, isopropyl, tertiary-butyl, cyclopentyl, cyclopentylmethyl, 4-fluorophenyl, 4-fluorophenyl-methyl, $CH_3(CH_2)_{16}$— or cis-$CH_3(CH_2)_7CH{=}CH(CH_2)_7$—.

4. A compound according to claim 1, which is a hydrochloride, (E)-but-2-enedioate or ethanedioate salt.

5. A process for preparing a compound as defined in claim 1, in which α-(4-chlorophenyl)-4-[(4-fluorophenyl)methyl]piperidine-1-ethanol is reacted with an anhydride of formula $(RCO)_2O$ or an acid chloride of formula RCOCl, in which R is as defined in claim 1.

6. A pharmaceutical composition which comprises a compound as defined in claim 1, in association with an excipient.

7. A compound as defined in claim 1, for use in a method of treatment of the human or animal body.

8. A method of treating a subject requiring the administration of a neuroprotective or neurotrophic agent which comprises administering to that subject an effective amount of a compound as defined in claim 1.

* * * * *